(12) United States Patent
Deefholts

(10) Patent No.: US 9,000,319 B2
(45) Date of Patent: Apr. 7, 2015

(54) SORTING METHOD AND APPARATUS

(75) Inventor: Benedict Deefholts, London (GB)

(73) Assignee: Buhler Sortex Ltd, London (GB)

( * ) Notice: Subject to any disclaimer, the term of this patent is extended or adjusted under 35 U.S.C. 154(b) by 367 days.

(21) Appl. No.: 13/141,863

(22) PCT Filed: Dec. 21, 2009

(86) PCT No.: PCT/GB2009/002931
§ 371 (c)(1),
(2), (4) Date: Dec. 19, 2011

(87) PCT Pub. No.: WO2010/073004
PCT Pub. Date: Jul. 1, 2010

(65) Prior Publication Data
US 2012/0074047 A1    Mar. 29, 2012

(30) Foreign Application Priority Data
Dec. 23, 2008 (GB) .................................. 0823419.7

(51) Int. Cl.
*B07C 5/00* (2006.01)
*B07C 5/36* (2006.01)
*B07C 5/342* (2006.01)
(Continued)

(52) U.S. Cl.
CPC .................. *B07C 5/368* (2013.01); *B07C 5/342* (2013.01); *G01N 21/314* (2013.01); *G01N 21/85* (2013.01); *G01N 33/025* (2013.01); *G01N 21/359* (2013.01); *G01N 21/94* (2013.01); *G01N 2021/8592* (2013.01); *G01N 2201/0618* (2013.01); *Y10S 209/939* (2013.01)
209/939

(58) Field of Classification Search
USPC .......................... 209/576, 577, 582, 587, 939
See application file for complete search history.

(56) References Cited

U.S. PATENT DOCUMENTS 4,236,640 A * 12/1980 Knight .......................... 209/587
4,369,886 A * 1/1983 Lane et al. .................... 209/564
(Continued)

FOREIGN PATENT DOCUMENTS

CN     1130104 A    9/1996
CN     1354627 A    6/2002
(Continued)

OTHER PUBLICATIONS

International Search Report for corresponding application No. PCT/GB2009/002931 dated Mar. 30, 2010.
(Continued)

*Primary Examiner* — Prasad Gokhale
(74) *Attorney, Agent, or Firm* — Renner, Otto, Boisselle & Sklar, LLP

(57) ABSTRACT

A method of and apparatus for sorting foreign matter from a flow, the method comprising the steps of: identifying objects within a flow; for each identified object, determining reflectance intensities at at least two different wavelengths or ranges of wavelengths; and for each identified object, comparing the reflectance intensities at the at least two different wavelengths or ranges of wavelengths to a reference intensity profile, wherein the identified object is characterized as foreign matter when the reflectance intensities at the at least two different wavelengths or ranges of wavelengths fall within a predetermined region of the reference intensity profile.

29 Claims, 5 Drawing Sheets

Figure 1:
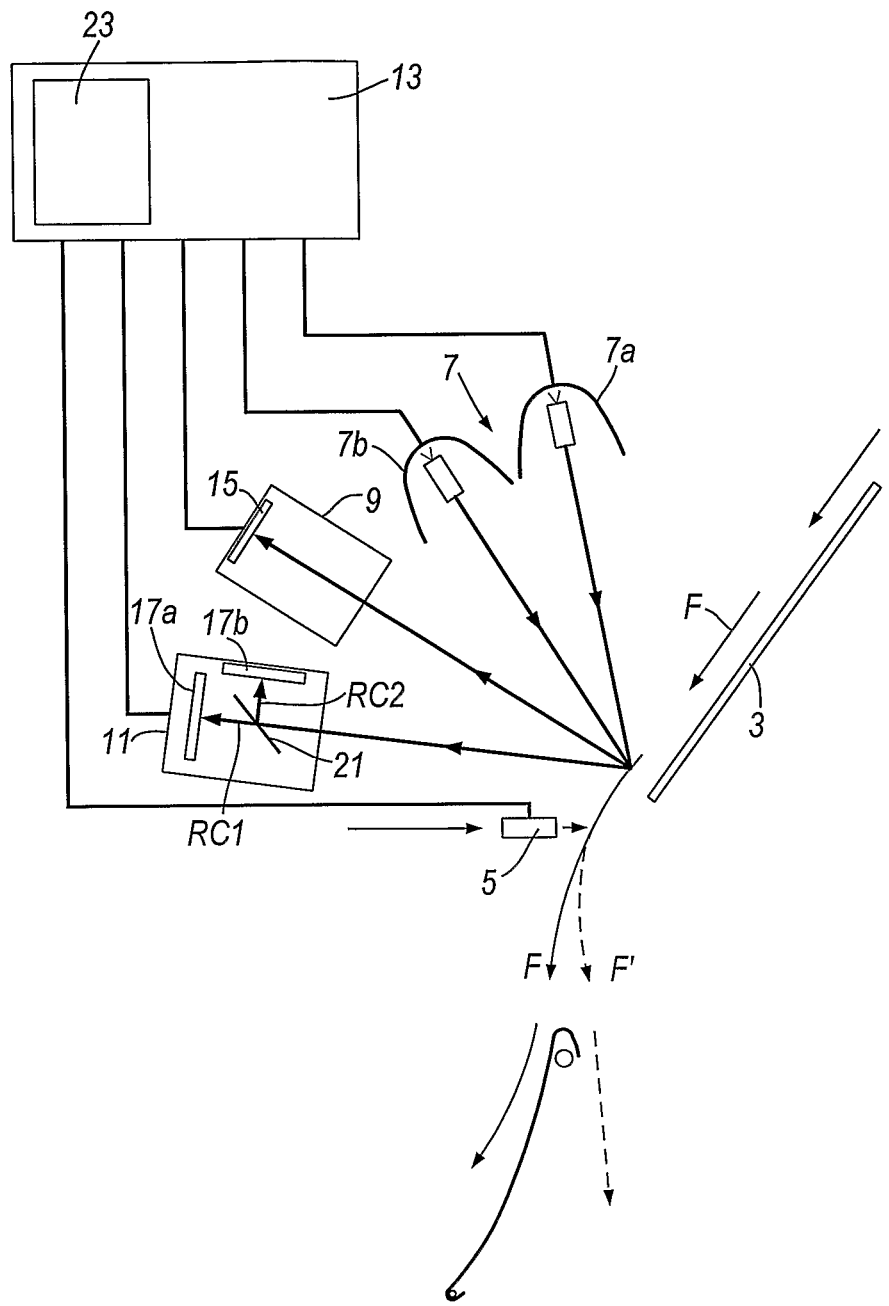

(51) Int. Cl.
*G01N 21/31* (2006.01)
*G01N 21/85* (2006.01)
*G01N 33/02* (2006.01)
G01N 21/359 (2014.01)
G01N 21/94 (2006.01)

(56) References Cited

U.S. PATENT DOCUMENTS

| | | | |
|---|---|---|---|
| 5,353,937 A | 10/1994 | Childress | |
| 5,675,416 A * | 10/1997 | Campbell et al. | 356/367 |
| 5,779,058 A | 7/1998 | Satake et al. | |
| 5,794,788 A | 8/1998 | Massen | |
| 5,873,470 A * | 2/1999 | Davis et al. | 209/555 |
| 6,060,677 A * | 5/2000 | Ulrichsen et al. | 209/577 |
| 6,506,991 B1 * | 1/2003 | Eixelberger et al. | 209/581 |
| 6,646,218 B1 * | 11/2003 | Campbell et al. | 209/582 |
| 6,791,683 B2 * | 9/2004 | Sjodin | 356/326 |
| 7,081,594 B1 * | 7/2006 | Khalfan et al. | 209/578 |
| 7,842,896 B1 * | 11/2010 | Calcoen et al. | 209/576 |
| 2002/0008055 A1 * | 1/2002 | Campbell et al. | 209/577 |
| 2008/0035532 A1 * | 2/2008 | Hunter et al. | 209/3.3 |
| 2009/0032445 A1 * | 2/2009 | Doak et al. | 209/587 |
| 2012/0021101 A1 * | 1/2012 | Berghmans et al. | 426/231 |

FOREIGN PATENT DOCUMENTS

| | | | |
|---|---|---|---|
| EP | 341096 A2 * | 11/1989 | B07C 5/342 |
| EP | 0 719 598 A2 | 7/1996 | |
| EP | 1 188 385 A1 | 3/2002 | |
| EP | 1188385 | 3/2002 | |
| GB | 1144779 | 3/1969 | |
| GB | 1 604 595 | 12/1981 | |
| GB | 2 119 509 A | 11/1983 | |
| JP | 2005-028302 A | 2/2005 | |
| WO | 00/57160 | 9/2000 | |
| WO | 00/58035 | 10/2000 | |

OTHER PUBLICATIONS

Tatzer et al., "Industrial application for inline material sorting using hyperspectral imagining in the NIR range", Real-Time Imagining, vol. 11, 2005, pp. 99-107.

* cited by examiner

SORTING METHOD AND APPARATUS

This application is a national phase of International Application No. PCT/GB2009/002931 filed Dec. 21, 2009 and published in the English language.

The present invention relates to a sorting method and apparatus for sorting foreign matter, such as wood, cardboard, plastics and rubber materials, including liner and glove materials, from foodstuffs, in particular frozen foodstuffs, and especially frozen vegetable matter.

Existing apparatus utilize laser-based sorters to identify foreign matter from frozen foodstuffs. These apparatus suffer from the particular problem, however, that the vision settings have to be changed for each different type of foodstuff to be sorted, in order to discern between the foodstuff and foreign matter. This need to alter the vision settings for each foodstuff is particularly problematic, in that operators can forget to alter the vision settings or use an incorrect setting, which leads to inadequate sorting. Also, laser sorters are not particularly effective in sorting certain kinds of foodstuffs, because of the emitted radiation being a combination of diffusion and reflectance.

Apparatus have been developed which image visible and infra-red (IR) reflectance, but these apparatus also suffer from the disadvantage of requiring configuration for each type of foodstuff to be sorted, and suffer particularly in not being able to discern between certain kinds of foodstuff and foreign matter, with one example being borlotti bean.

The present inventor has developed a sorting method and apparatus which, for a broad range of foodstuffs, allows for the sorting of foreign matter without any re-configuration of the vision settings.

As will be appreciated, the ability to sort foreign matter from a wide range of foodstuffs without machine re-configuration is particularly advantageous, in avoiding the possibility of an incorrect setting being utilized which would lead to poor or ineffective sorting.

In one aspect the present invention provides a method of sorting foreign matter from a flow, the method comprising the steps of: identifying objects within a flow; for each identified object, determining reflectance intensities at at least two different wavelengths or ranges of wavelengths; and for each identified object, comparing the reflectance intensities at the at least two different wavelengths or ranges of wavelengths to a reference intensity profile, wherein the identified object is characterized as foreign matter when the reflectance intensities at the at least two different wavelengths or ranges of wavelengths fall within a predetermined region of the reference intensity profile.

In one embodiment the flow is of a foodstuff.

In one embodiment the foodstuff is vegetable matter.

In one embodiment the foodstuff is frozen.

In one embodiment the step of identifying objects comprises the steps of: acquiring images of the flow; and processing the images to identify objects within the flow.

In one embodiment the images are outside the visible spectrum in the near infra-red (NIR) to short wavelength infra-red (SWIR) spectrum.

In one embodiment the step of determining reflectance intensities comprises, for each identified object, the steps of: determining a first reflectance intensity from the identified object at a first wavelength in the range of from about 800 nm to about 1200 nm; and determining a second reflectance intensity from the identified object at a second wavelength in the range of from about 1470 nm to about 1570 nm.

In one embodiment the first wavelength is in the range of from about 850 nm to about 1110 nm.

In one embodiment the first wavelength is in the range of from about 850 nm to about 900 nm.

In one embodiment the first wavelength is about 850 nm.

In one embodiment the second wavelength is about 1470 nm.

In one embodiment the reference intensity profile is represented by a multi-dimensional intensity diagram, a discrete region of which represents foreign matter.

In one embodiment the method further comprises the step of: illuminating the flow with at least one illumination source.

In one embodiment the at least one illumination source provides illumination in the visible to short wavelength infra-red (SWIR) spectrum.

In one embodiment the at least one illumination source comprises a halogen lamp.

In one embodiment the method further comprises the step of: deflecting objects identified as foreign matter from the flow.

In another aspect the present invention provides a sorting apparatus for sorting foreign matter from a flow, the apparatus comprising: an illumination unit for illuminating a flow; a camera unit for imaging radiation reflected by objects in the flow, the camera unit including at least two detectors and at least one beam splitter, preferably a dichroic element, for splitting the reflected radiation into at least first and second reflected components, which have different wavelengths or ranges of wavelengths and are detected by respective ones of the detectors; and a processing unit which is operative to identify objects within the flow, and, for each identified object, compare the reflectance intensities at the at least two different wavelengths or ranges of wavelengths to a reference intensity profile, wherein the identified object is characterized as foreign matter when the reflectance intensities at the at least two different wavelengths or ranges of wavelengths fall within a predetermined region of the reference intensity profile.

In one embodiment the flow is of a foodstuff.

In one embodiment the foodstuff is vegetable matter.

In one embodiment the foodstuff is frozen.

In one embodiment the illumination unit comprises at least one illumination source.

In one embodiment the at least one illumination source provides illumination in the visible to short wavelength infra-red (SWIR) spectrum.

In one embodiment the at least one illumination source comprises a halogen lamp.

In one embodiment the images are outside the visible spectrum in the near infra-red (NIR) to short wavelength infra-red (SWIR) spectrum.

In one embodiment the camera unit includes first and second detectors for detecting respectively, for each identified object, a first reflectance intensity from the identified object at a first wavelength in the range of from about 800 nm to about 1200 nm and a second reflectance intensity from the identified object at a second wavelength in the range of from about 1470 nm to about 1570 nm.

In one embodiment the first wavelength is in the range of from about 850 nm to about 1110 nm.

In one embodiment the first wavelength is in the range of from about 850 nm to about 900 nm.

In one embodiment the first wavelength is about 850 nm.

In one embodiment the second wavelength is about 1470 nm.

In one embodiment the reference intensity profile is represented by a multi-dimensional intensity diagram, a discrete region of which represents foreign matter.

In one embodiment the apparatus further comprises: a deflector for deflecting objects identified as foreign matter from the flow.

Figure 2:
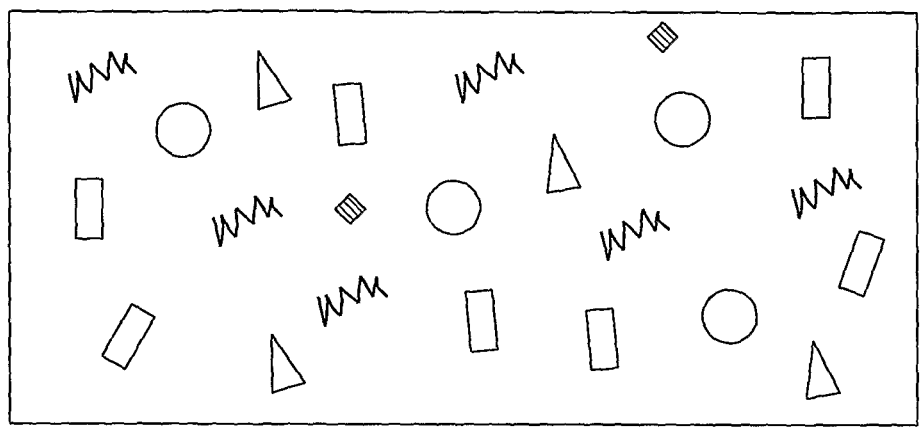
Figure 3:
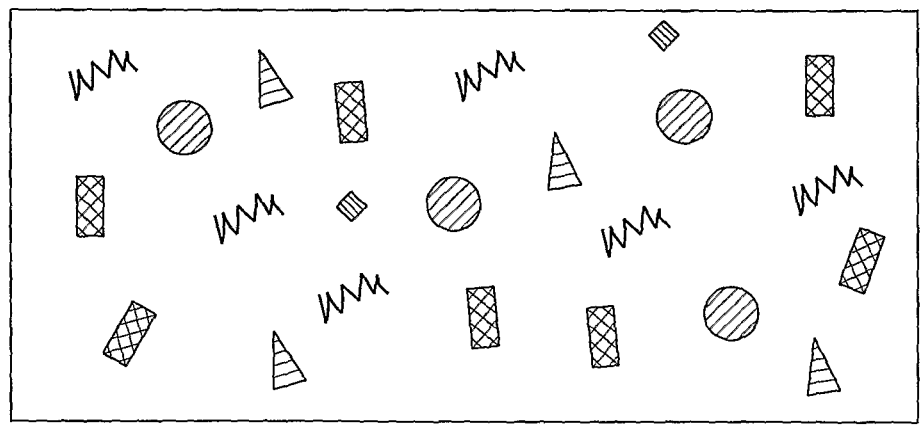
Figure 4:
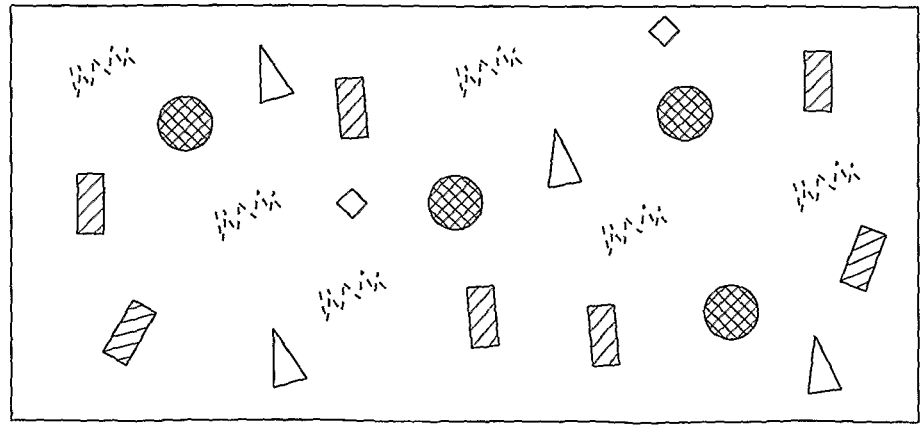
Figure 5:
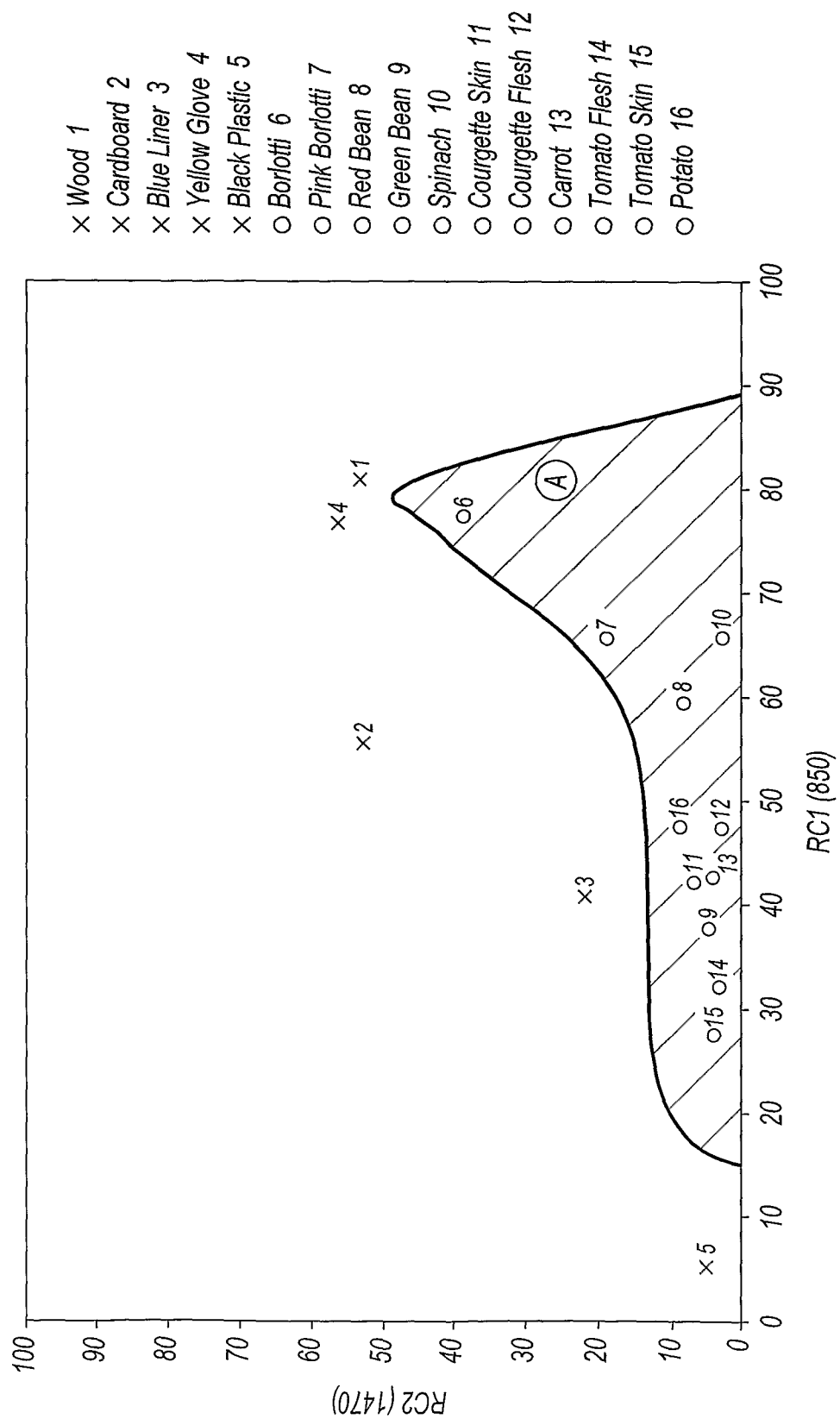
Figure 6:
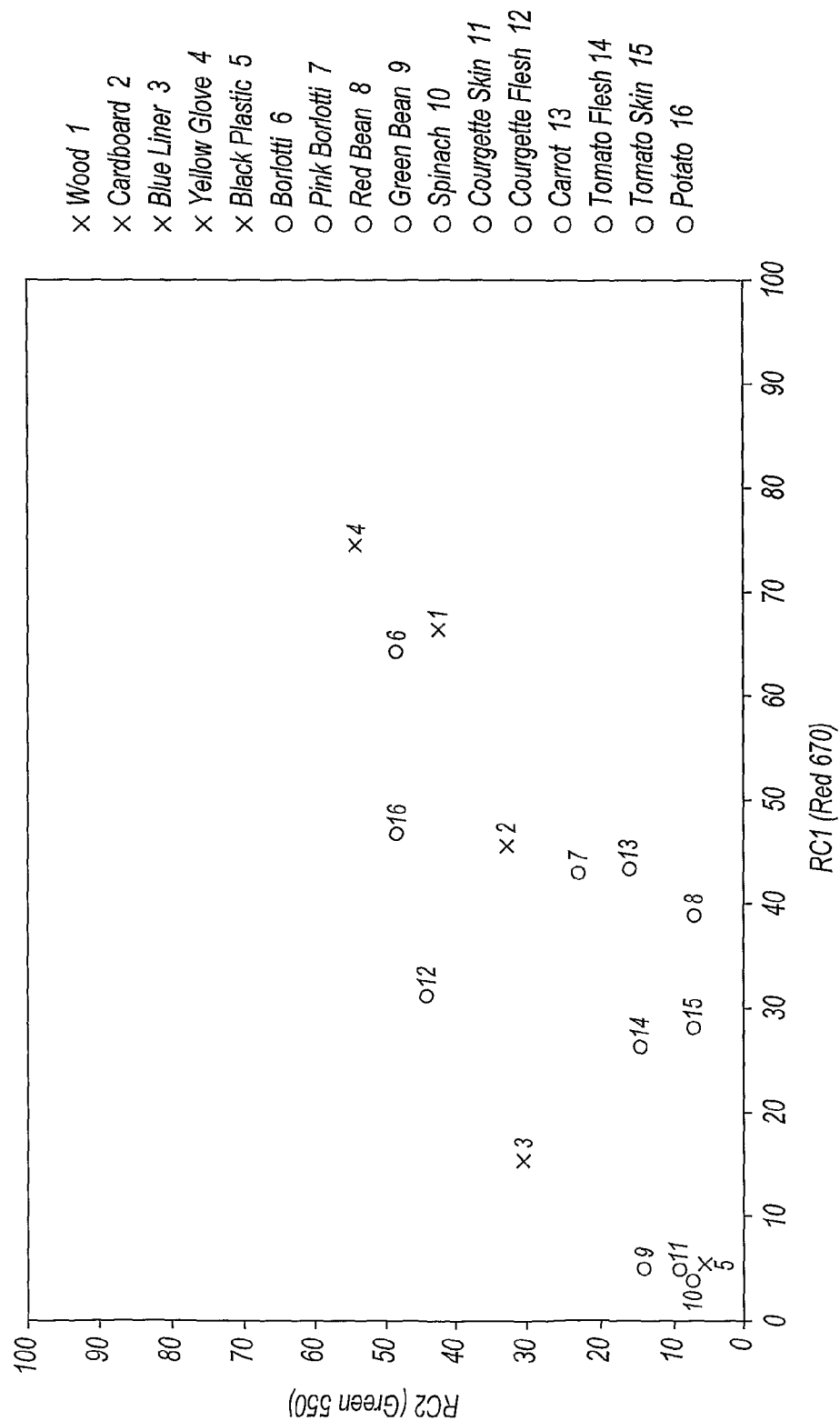
Figure 7:
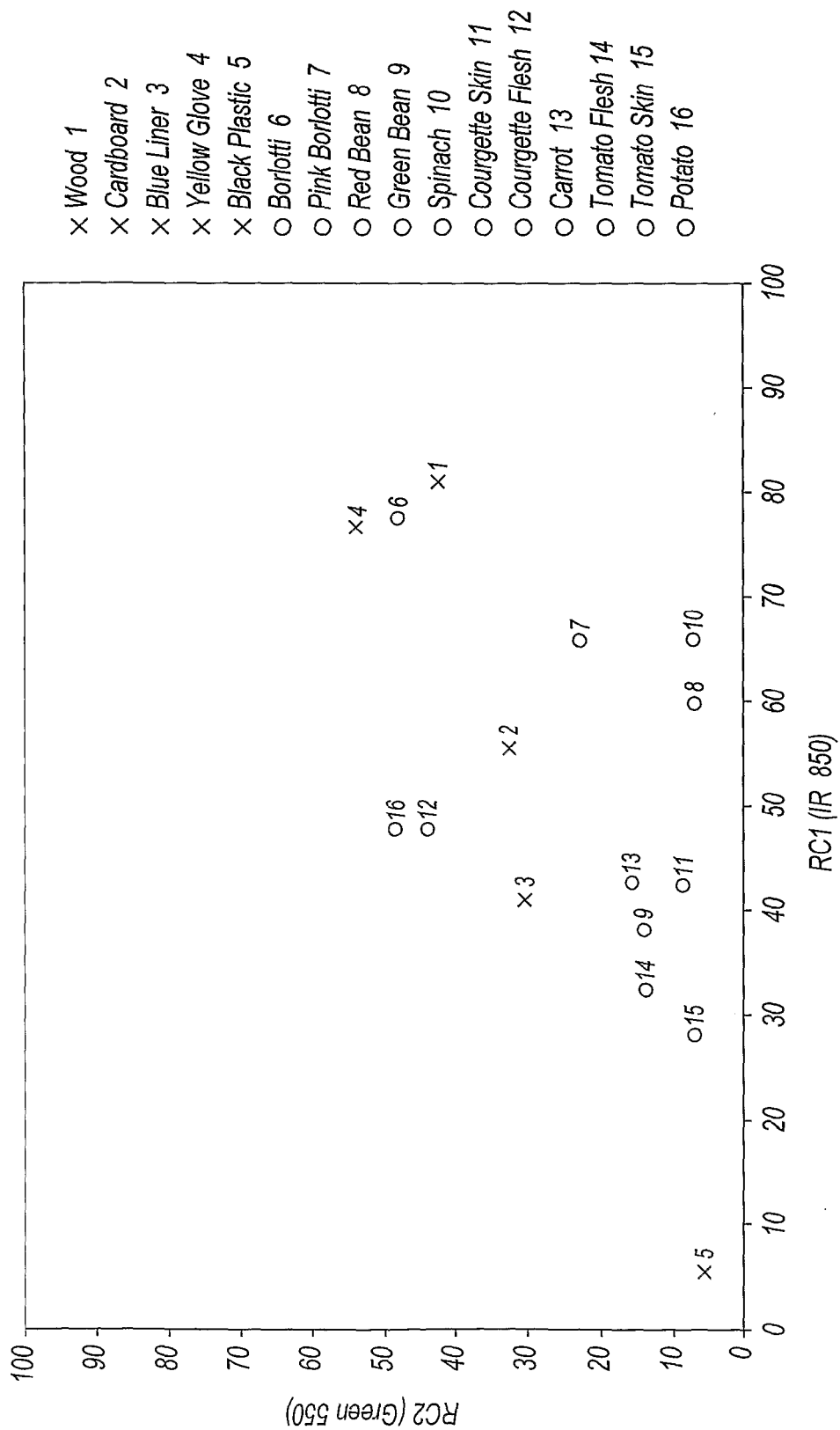

A preferred embodiment of the present invention will now be described hereinbelow by way of example only with reference to the accompanying drawings, in which:

FIG. 1 schematically represents a sorting apparatus in accordance with a preferred embodiment of the present invention;

FIG. 2 schematically represents a visible image acquired by the first camera unit of the sorting apparatus;

FIG. 3 schematically represents an intensity image acquired by the first detector of the second camera unit of the sorting apparatus;

FIG. 4 schematically represents an intensity image acquired by the second detector of the second camera unit of the sorting apparatus;

FIG. 5 illustrates an intensity-intensity diagram of the reflectance intensities at the detection wavelengths 850 nm and 1470 nm for different vegetable matter in a vegetable mix and various foreign matter in accordance with one embodiment of the present invention;

FIG. 6 illustrates a comparative intensity-intensity diagram of the reflectance intensities for the detection wavelengths 550 nm and 670 nm for different vegetable matter in a vegetable mix and various foreign matter; and FIG. 7 illustrates another comparative intensity-intensity diagram of the reflectance intensities for the detection wavelengths 550 nm and 850 nm for different vegetable matter in a vegetable mix and various foreign matter.

The sorting apparatus includes a chute 3 along which a flow F of a foodstuff, in this embodiment a vegetable mix, is delivered, typically as supplied from a storage container, a deflector 5 which is operative to deflect objects identified as foreign matter from the flow F, an illumination unit 7 for illuminating the flow F, a first camera unit 9 for acquiring images of the flow F to enable determination of the color and shape of objects within the flow F, a second camera unit 11 for acquiring at least two reflectance intensity images of the flow F to enable characterization of objects within the flow F, and a control unit 13 for identifying objects as foreign matter from the acquired images and operating the deflector 5 to deflect the objects identified as foreign matter from the flow F.

In this embodiment the foodstuff is vegetable matter, here frozen vegetable matter in a vegetable mix, which may include foreign matter. Examples of vegetable matter include bean, such as borlotti, pink borlotti, red bean and green bean, spinach, courgette skin, courgette flesh, carrot, tomato skin, tomato flesh, potato, celery, lentil, such as yellow lentil. Examples of foreign matter include wood, cardboard, plastics materials, including blue liner and black plastic, and rubber materials, including glove material, such as yellow gloves.

In this embodiment the deflector 5 is a pneumatic deflector, which comprises an elongate bar which extends laterally across the width of the chute 3 and includes a plurality of separately-operable air jets along the length of the bar. By selective operation of the air jets, objects which are identified as foreign matter are deflected from the flow F into a separate waste flow F'.

In this embodiment the illumination unit 7 comprises first and second illumination sources 7a, 7b, here halogen lamps, which emit radiation over a broad spectrum from the visible to the short wavelength infra-red (SWIR) spectrum, here wavelengths in the range of about 400 nm to about 2000 nm. In an alternative embodiment the illumination sources 7a, 7b could be of different kind so as to be optimized for respective ones of the first and second camera units 9, 11.

In this embodiment the first camera unit 9 comprises a detector 15, here a visible light detector, for acquiring images of the flow F in the visible spectrum, as represented in FIG. 2, which, using conventional vision processing, enables identification of the color and shape of objects within the flow F, if required.

In this embodiment the second camera unit 11 comprises first and second detectors 17a, 17b, here InGaAs detectors, and a beam splitter 21, here a dichroic element, for splitting the reflected radiation into first and second reflected components RC1, RC2 having different wavelengths $\lambda 1$, $\lambda 2$, which are detected by respective ones of the detectors 17a, 17b. With this arrangement, the detectors 17a, 17b each provide a reflected intensity image at the respective detection wavelength $\lambda 1$, $\lambda 2$, as illustrated in FIGS. 3 and 4.

In this embodiment the dichroic element 21 comprises a prism, but in another embodiment could be provided by a mirror.

In this embodiment the first reflected component RC1 has a wavelength $\lambda 1$ in the range of from about 800 nm to about 1200 nm, preferably from about 850 nm to about 1110 nm, more preferably from about 850 nm to about 900 nm, and still more preferably about 850 nm.

In this embodiment the second reflected component RC2 has a wavelength $\lambda 2$ in the range of from about 1470 nm to about 1570 nm, and more preferably about 1470 nm.

In this embodiment the control unit 13 includes a vision processor 23, which processes the visible images acquired by the first camera unit 9 to determine the color and shape of objects within the flow F, as required, and the intensity images acquired by the second camera unit 11, utilizing a look-up function, graphically represented as a two-dimensional intensity-intensity diagram in FIG. 5, to characterize objects within the flow F. As represented in FIG. 5 for the selected detection wavelengths, the vegetable matter is characterized within a discrete region A of the intensity-intensity diagram, with all of the foreign matter falling out of this region A, and, using this intensity-intensity diagram, the objects within the flow F are characterized as vegetable matter or foreign matter. Where an object is identified as foreign matter, the control unit 13 operates the deflector 5, as described above, to deflect that object into a waste flow F'.

Through the selection of the specific detection wavelengths $\lambda 1$, $\lambda 2$, the sorting apparatus enables the identification of foreign matter from a wide range of vegetable matter, and, indeed, all vegetable matter investigated to date, without requiring any machine re-configuration. This has not been possible previously, and, indeed, is contrary to the understanding in the field of art, which is to the need for re-configuration of the vision settings in order to achieve optimal sorting. As discussed above, the ability to sort different mixes of vegetable matter without requiring any machine re-configuration is particularly advantageous, in avoiding the possibility of an incorrect setting being utilized which would lead to poor or ineffective sorting.

By way of comparison, FIGS. 6 and 7 illustrate intensity-intensity diagrams for other detection wavelengths, that is, 550 nm and 670 nm and 550 nm and 850 nm, respectively. As can be clearly observed, at these detection wavelengths, vegetable matter cannot be discerned from foreign matter, as the reflectance intensity profile of vegetable matter is bounded by that of foreign matter.

Finally, it will be understood that the present invention has been described in its preferred embodiment and can be modified in many different ways without departing from the scope of the invention as defined by the appended claims.

In one modification, the second camera unit 11 could include three or more detectors 17, which, through the use of one or more further dichroic elements 21, detect reflected radiation components at three or more detection wavelengths. Where the second camera unit 11 includes three detectors 17 for detecting reflected radiation components at three wavelengths, the intensity diagram is represented by a three-sided diagram.

The invention claimed is:

1. A method of sorting foreign matter from a flow, the method comprising the steps of:
   identifying objects within a flow;
   for each identified object, determining reflectance intensities at at least two different wavelengths or ranges of wavelengths; and
   for each identified object, comparing the reflectance intensities at a first reflectance intensity from the identified object at a first wavelength in the range of from about 800 nm to about 1200 nm and a second reflectance intensity from the identified object at a second wavelength in the range of from about 1470 nm to about 1570 nm to a reference intensity profile, wherein the identified object is characterized as foreign matter when the reflectance intensities at the at least two different wavelengths or ranges of wavelengths fall within a predetermined region of the reference intensity profile.

2. The method of claim 1, wherein the flow is of a foodstuff.

3. The method of claim 2, wherein the foodstuff is vegetable matter.

4. The method of claim 2, wherein the foodstuff is frozen.

5. The method of claim 1, wherein the step of identifying objects comprises the steps of:
   acquiring images of the flow; and
   processing the images to identify objects within the flow.

6. The method of claim 5, wherein the images are outside the visible spectrum in the near infra-red (NIR) to short wavelength infra-red (SWIR) spectrum.

7. The method of claim 1, wherein the first wavelength is in the range of from about 850 nm to about 1110 nm.

8. The method of claim 1, wherein the first wavelength is in the range of about 850 nm to about 900 nm.

9. The method of claim 1, wherein the first wavelength is about 850 nm.

10. The method of claim 1, wherein the second wavelength is about 1470 nm.

11. The method of claim 1, wherein the reference intensity profile is represented by an intensity diagram, a discrete region of which represents foreign matter.

12. The method of claim 1, further comprising the step of:
    illuminating the flow with at least one illumination source.

13. The method of claim 12, wherein the at least one illumination source provides illumination in the visible to short wavelength infra-red (SWIR) spectrum.

14. The method of claim 13, wherein the at least one illumination source comprises a halogen lamp.

15. The method of claim 1, further comprising the step of:
    deflecting objects identified as foreign matter from the flow.

16. A sorting apparatus for sorting foreign matter from a flow, the apparatus comprising:
    an illumination unit for illuminating a flow;
    a camera unit for imaging radiation reflected by objects in the flow, the camera unit including first and second detectors for detecting respectively, for each identified object, a first reflectance intensity from the identified object at a first wavelength in the range of from about 800 nm to about 1200 nm and a second reflectance intensity from the identified object at a second wavelength in the range of from about 1470 nm to about 1570 nm, and at least one beam splitter for splitting the reflected radiation into at least first and second reflected components, which have different wavelengths or ranges of wavelengths and are detected by respective ones of the detectors; and
    a processing unit which is operative to identify objects within the flow, and, for each identified object, compare the reflectance intensities at the at least two different wavelengths or ranges of wavelengths to a reference intensity profile, wherein the identified object is characterized as foreign matter when the reflectance intensities at the at least two different wavelengths or ranges of wavelengths fall within a predetermined region of the reference intensity profile.

17. The apparatus of claim 16, wherein the flow is of a foodstuff.

18. The apparatus of claim 17, wherein the foodstuff is vegetable matter.

19. The apparatus of claim 17, wherein the foodstuff is frozen.

20. The apparatus of claim 16, wherein the illumination unit comprises at least one illumination source.

21. The apparatus of claim 20, wherein the at least one illumination source provides illumination in the visible to short wavelength infra-red (SWIR) spectrum.

22. The apparatus of claim 20, wherein the at least one illumination source comprises a halogen lamp.

23. The apparatus of claim 16, wherein the images are outside the visible spectrum in the near infra-red (NIR) to short wavelength infra-red (SWIR) spectrum.

24. The apparatus of claim 16, wherein the first wavelength is in the range of from about 850 nm to about 1110 nm.

25. The apparatus of claim 16, wherein the first wavelength is in the range of from about 850 nm to about 900 nm.

26. The apparatus of claim 16, wherein the first wavelength is about 850 nm.

27. The apparatus of claim 16, wherein the second wavelength is about 1470 nm.

28. The apparatus of claim 16, wherein the reference intensity profile is represented by an intensity diagram, a discrete region of which represents foreign matter.

29. The apparatus of claim 16, further comprising:
    a deflector for deflecting objects identified as foreign matter from the flow.

* * * * *